(12) United States Patent
Okuda et al.

(10) Patent No.: US 8,792,959 B2
(45) Date of Patent: Jul. 29, 2014

(54) BIOLOGICAL INFORMATION DETECTION DEVICE

(71) Applicant: Seiko Instruments Inc., Chiba (JP)

(72) Inventors: Hideki Okuda, Chiba (JP); Teruo Kato, Chiba (JP); Dai Terasawa, Chiba (JP); Takahiro Kaneko, Chiba (JP); Hiroshi Kawamata, Chiba (JP); Nobukazu Omori, Chiba (JP); Hideaki Koshoji, Chiba (JP)

(73) Assignee: Seiko Instruments Inc. (JP)

( * ) Notice: Subject to any disclaimer, the term of this patent is extended or adjusted under 35 U.S.C. 154(b) by 8 days.

(21) Appl. No.: 13/669,808

(22) Filed: Nov. 6, 2012

(65) Prior Publication Data

US 2013/0158380 A1     Jun. 20, 2013

(30) Foreign Application Priority Data

Nov. 8, 2011   (JP) ................................ 2011-244574

(51) Int. Cl.
*A61B 5/0402* (2006.01)
*A61B 5/0408* (2006.01)

(52) U.S. Cl.
USPC .......................................... 600/390; 600/509

(58) Field of Classification Search
USPC ................................................ 600/390, 509
See application file for complete search history.

(56) References Cited

U.S. PATENT DOCUMENTS

| | | | | |
|---|---|---|---|---|
| 4,809,700 A * | 3/1989 | Castelli | ......................... | 600/384 |
| 4,889,131 A * | 12/1989 | Salem et al. | .................. | 600/484 |
| 5,491,474 A * | 2/1996 | Suni et al. | ................ | 340/870.31 |
| 5,778,880 A * | 7/1998 | Chen | ............................. | 600/509 |
| 6,272,365 B1 * | 8/2001 | Ronkainen et al. | ............ | 600/390 |
| 6,553,247 B1 * | 4/2003 | Rytky | ............................ | 600/386 |
| 6,600,942 B2 * | 7/2003 | Nissila et al. | ................ | 600/372 |
| 7,039,456 B2 * | 5/2006 | Chen | ............................. | 600/509 |
| 7,167,737 B2 * | 1/2007 | Fujii et al. | ..................... | 600/390 |
| 7,526,840 B2 | 5/2009 | Pernu et al. | ..................... | 24/265 |
| D603,521 S | 11/2009 | Lindberg et al. | ............. | D24/187 |
| 8,060,191 B2 * | 11/2011 | Chen | ............................. | 600/509 |
| 2006/0058695 A1 * | 3/2006 | Chen | ............................. | 600/509 |
| 2007/0093707 A1 * | 4/2007 | Noguchi | ........................ | 600/390 |
| 2009/0099472 A1 * | 4/2009 | Remmert et al. | ............. | 600/534 |
| 2010/0191090 A1 * | 7/2010 | Shin et al. | ..................... | 600/388 |

* cited by examiner

*Primary Examiner* — Lee S Cohen
(74) *Attorney, Agent, or Firm* — Adams & Wilks

(57) ABSTRACT

A biological information detection device has a device main body and a biological signal detection portion formed integrally with the device main body. The detection portion has at least one electrode for contacting a biological surface of a human body. A mounting portion mounts the main body and the detection portion to a human body without the mounting portion being directly attached to the detection portion. The main body and the detection portion are integrally connected by a mechanical connection portion that mechanically connects the main body and the detection portion to each other, and by an electrical connection portion that electrically connects the main body and the electrode of the detection portion to each other. The mechanical connection portion and the electrical connection portion are positioned relative one another so as not to be arranged alongside a load direction of an external force acting on the mechanical connection portion.

20 Claims, 11 Drawing Sheets

BIOLOGICAL INFORMATION DETECTION DEVICE

BACKGROUND OF THE INVENTION

1. Field of the Invention

The present invention relates to a biological information detection device that detects a biological signal by installing an electrode on the biological surface of the human body.

2. Background Art

Among these kinds of biological information detection devices, there is, for example, a heartbeat measurement device that detects an electro-cardiac signal generated in association with a heartbeat, and measures a heart rate from the biological surface. As such a heartbeat measurement device, there is, for example, a device which includes a main body portion having a detection circuit board and the like built-in, and a strap which mounts the main body portion to the human body, the strap being provided with a pair of electrodes. The main body portion and the strap are provided with an electrical connection portion for electrically connecting a detection circuit board of the main body portion to an electrode of the strap.

Based on such a configuration, an electro-cardiac signal generated in association with a heartbeat is detected by bringing a pair of electrodes into contact with the chest (biological surface) of the human body, and the main body portion derives a heart rate on the basis of the detected electro-cardiac signal.

Further, among the heartbeat measurement devices, there is, for example, a device in which the main body portion is detachably provided to the strap from the viewpoint of maintenance such as cleaning of the strap. When the main body portion is mounted to the strap, the electrical connection portion provided to the strap and the electrical connection portion provided to the main body portion are mechanically connected to each other, and the detection circuit board and the electrode are electrically connected to each other (see, for example, Specification of U.S. Pat. No. 7,526,840 and Design Registration U.S. Pat. No. 603,521).

However, in the above-mentioned related art, since the main body portion and the electrode are formed detachably to each other, there is a problem that the detection performance of the heartbeat measurement device becomes unstable depending on the installation conditions of the electrical connection portion. In addition, there is a concern that the electrical connection portion is damaged by repeatedly performing attaching and detaching operations of the main body portion and the electrode.

Further, since the strap is provided with an electrode, an external force in the tensile direction is applied to the electrode and the electrical connection portion at all times, in a state where the heartbeat measurement device is installed on the human body. For this reason, there is a concern that the electrical connection portion provided to the strap and the electrical connection portion provided to the main body portion is mechanically separated from each other, and thus the electrical connection between the detection circuit board and the electrode are cut off. In addition to this, there is a concern that the electrical connection portion is exposed to a cleaning solution in association with cleaning of the strap at the time of maintenance, resulting in damage.

Consequently, the present invention is contrived in view of such circumstances, and an object thereof is to provide a biological information detection device capable of preventing defects from occurring in an electrical connection portion while securing good maintenance, and preventing the detection performance from becoming unstable.

SUMMARY OF THE INVENTION

According to an aspect of the present invention, there is provided a biological information detection device including: a device main body: a biological signal detection portion, formed integrally with the device main body, which has an electrode that comes into contact with a biological surface; and a fixing portion, detachably provided to the device main body, which mounts the device main body and the biological signal detection portion to a human body, wherein the device main body and the biological signal detection portion are integrally provided through a mechanical connection portion that mechanically connects the device main body and the biological signal detection portion to each other, and an electrical connection portion that electrically connects the device main body and the electrode of the biological signal detection portion to each other, and a relative positional relationship between the mechanical connection portion and the electrical connection portion is set so as not to be arranged alongside a load direction of external force acting on the mechanical connection portion.

In this manner, the biological signal detection portion is provided integrally with the device main body, and the fixing portion is detachably provided to the device main body, so that it is possible to separate the biological signal detection portion from the fixing portion. For this reason, even when external force in the tensile direction is applied to the fixing portion, it is possible to reliably suppress transmission of the external force to the biological signal detection portion.

Even when the external force is applied to the biological signal detection portion, it is possible to receive a load using the mechanical connection portion. Since the relative positional relationship between the mechanical connection portion and the electrical connection portion is set so as not to be arranged alongside the load direction of the external force acting on the mechanical connection portion, it is possible to suppress transmission of the load received by the mechanical connection portion to the electrical connection portion.

In addition, since the biological signal detection portion is able to be separated from the fixing portion, it is possible to perform cleaning of a simple fixing portion, for example, in cleaning at the time of maintenance, and to reliably prevent defects from occurring in the electrical connection portion.

In this manner, it is possible to prevent defects from occurring in the electrical connection portion while securing good maintenance, and to prevent the detection performance from becoming unstable.

In the biological information detection device according to the foregoing aspect, a side of a direction in which a load of the external force is applied rather than the electrical connection portion may be provided with a wall that receives the load.

In this manner, the wall receives a load due to external force, and thus it is possible to more reliably suppress the application of the external force to the electrical connection portion.

In the biological information detection device according to the foregoing aspect, an easily deformable portion which is easily elastically deformed may be provided between the mechanical connection portion and the electrical connection portion.

According to such a configuration, when the load received in the mechanical connection portion is transmitted to the electrical connection portion, the easily deformable portion is deformed, and the load is absorbed by the easily deformable portion. For this reason, it is possible to more reliably suppress the application of the external force to the electrical connection portion.

In the biological information detection device according to the foregoing aspect, the biological signal detection portion may be formed from conductive elastomer, and the conductive elastomer may serve as the electrode.

According to such a configuration, it is possible to easily elastically deform the biological signal detection portion, and to more reliably absorb a load due to the external force in the mechanical connection portion.

According to the present invention, the biological signal detection portion is provided integrally with the device main body, and the fixing portion is detachably provided to the device main body, so that it is possible to separate the biological signal detection portion from the fixing portion. For this reason, even when external force in the tensile direction is applied to the fixing portion, it is possible to reliably suppress transmission of the external force to the biological signal detection portion.

Even when the external force is applied to the biological signal detection portion, it is possible to receive a load using the mechanical connection portion. Since the relative positional relationship between the mechanical connection portion and the electrical connection portion is set so as not to be arranged alongside the load direction of the external force acting on the mechanical connection portion, it is possible to suppress transmission of the load received by the mechanical connection portion to the electrical connection portion.

In addition, since the biological signal detection portion is able to be separated from the fixing portion, it is possible to perform cleaning of a simple fixing portion, for example, in cleaning at the time of maintenance, and to reliably prevent defects from occurring in the electrical connection portion.

In this manner, it is possible to prevent defects from occurring in the electrical connection portion while securing good maintenance, and to prevent the detection performance from becoming unstable.

DETAILED DESCRIPTION OF THE INVENTION

First Embodiment

Heartbeat Measurement Device

Next, a first embodiment of the present invention will be described with reference to FIGS. 1 to 9.

Figure 1:
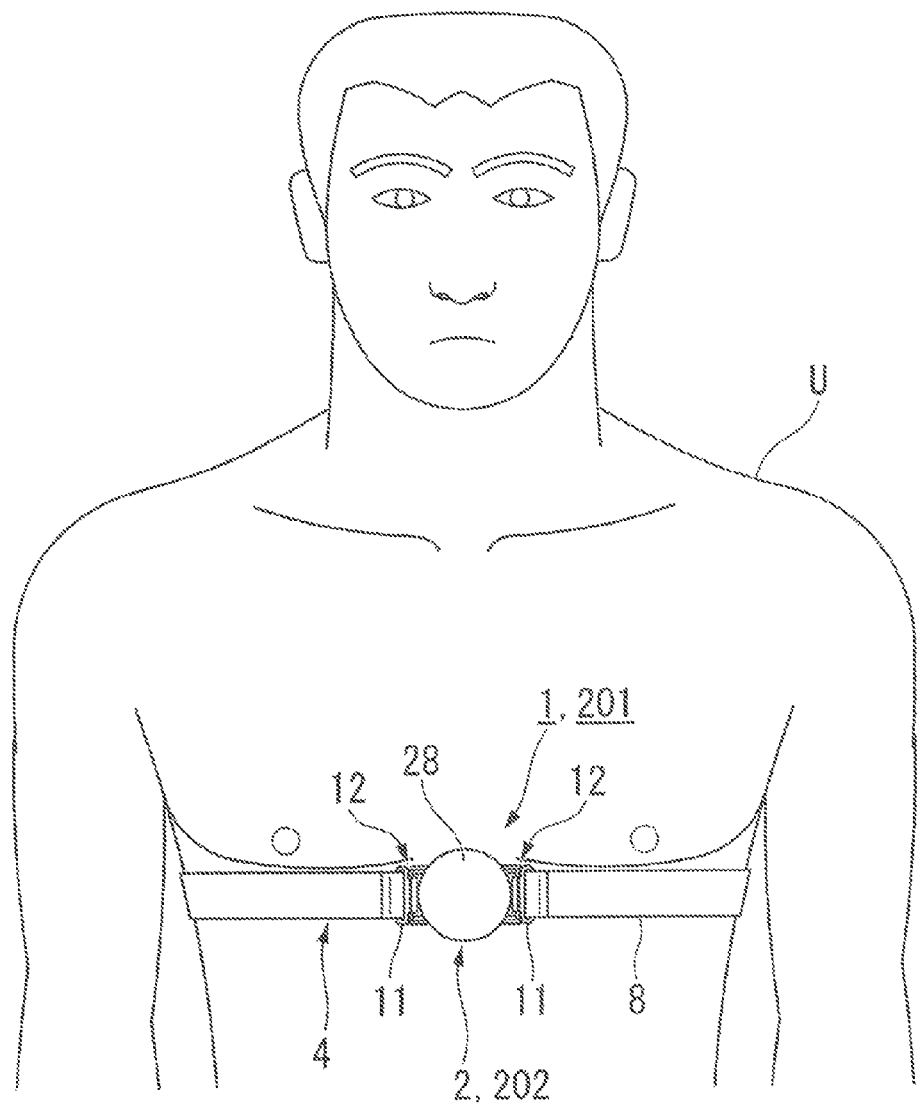
FIG. 1 is an explanatory diagram illustrating a state where a heartbeat measurement device according to a first embodiment of the present invention is installed on a user.
Figure 2:
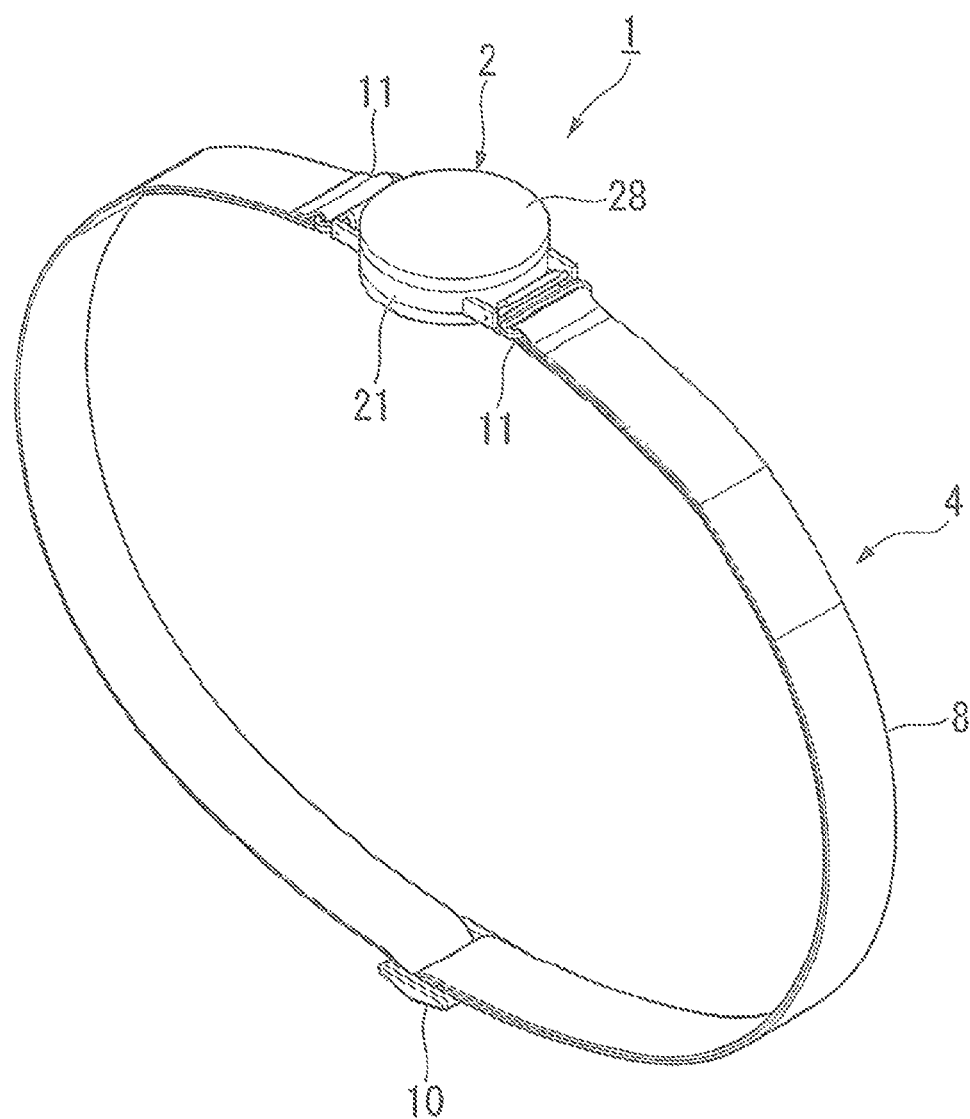
FIG. 2 is a perspective view illustrating the heartbeat measurement device according to the first embodiment of the present invention.
Figure 3:
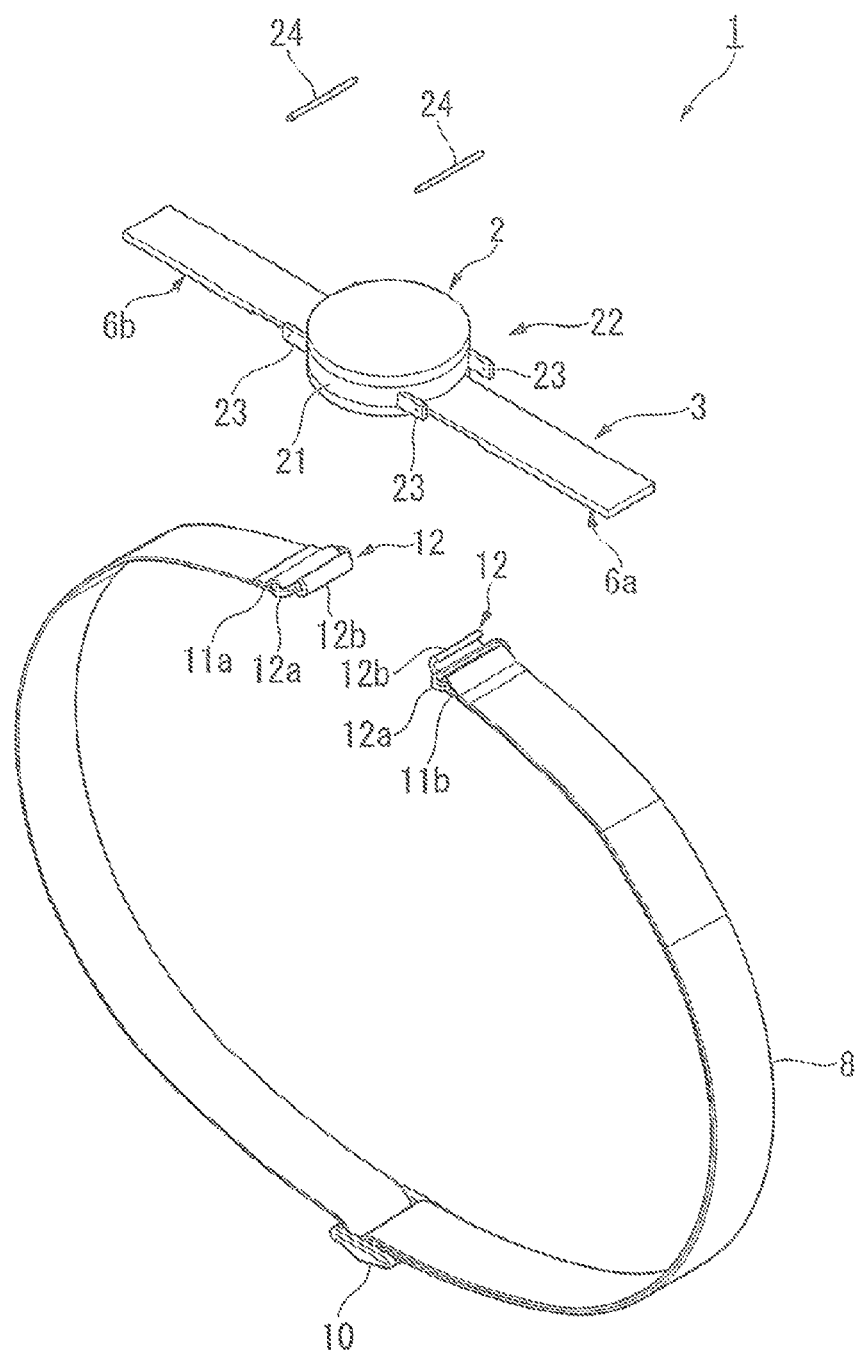
FIG. 3 is an exploded perspective view of a portion of the heartbeat measurement device according to the first embodiment of the present invention.

FIG. 1 is an explanatory diagram illustrating a state where a heartbeat measurement device 1 which is a biological information detection device according to the present invention is installed on a user U, FIG. 2 is a perspective view illustrating the heartbeat measurement device 1, and FIG. 3 is an exploded perspective view of a portion of the heartbeat measurement device 1.

Meanwhile, in the following description, the side which comes into contact with the user U in a state where the heartbeat measurement device 1 is mounted by the user U is expressed as the back side, and the surface on the side opposite to this back side and the side directed to the outside is expressed as the front side, and the like.

As shown in FIGS. 1 to 3, the heartbeat measurement device 1 is mounted to the chest which is a biological surface of the user U to detect an electro-cardiac signal generated in association with heartbeat, and wirelessly communicates the detected electro-cardiac signal. The heartbeat measurement device 1 includes a main body portion 2, a heartbeat detection portion 3 formed integrally with the main body portion 2, and a fixing band 4 (mounting portion) which mounts the main body portion 2 and the heartbeat detection portion 3 to the chest of the user U.

The fixing band 4 is formed in a substantially ring shape so as to be mounted over the whole circumference of the chest of the user U. More specifically, the fixing band 4 includes a strap 8 having elasticity which is formed in a substantially belt shape. Meanwhile, the strap 8 may not only be elastic, but also may be non-elastic.

A length adjustment member 10 for adjusting the length of the strap 8 is provided substantially at the center of the strap 8 in the long-side direction. In addition, ring portions 11 and 11 formed by folding back terminal portions of the strap 8 are respectively provided on both ends of the strap 8 in the long-side direction.

Two ring portions 11 and 11 are respectively provided with a strap attaching and detaching member 12. The strap attaching and detaching member 12 is constituted by a ring-shaped portion 12a inserted into the ring portions 11 and 11, and a hook portion 12b formed integrally with one side of the ring-shaped portion 12a. The hook portion 12b is engaged with the main body portion 2.

(Main Body Portion and Heartbeat Detection Portion)

Figure 4:
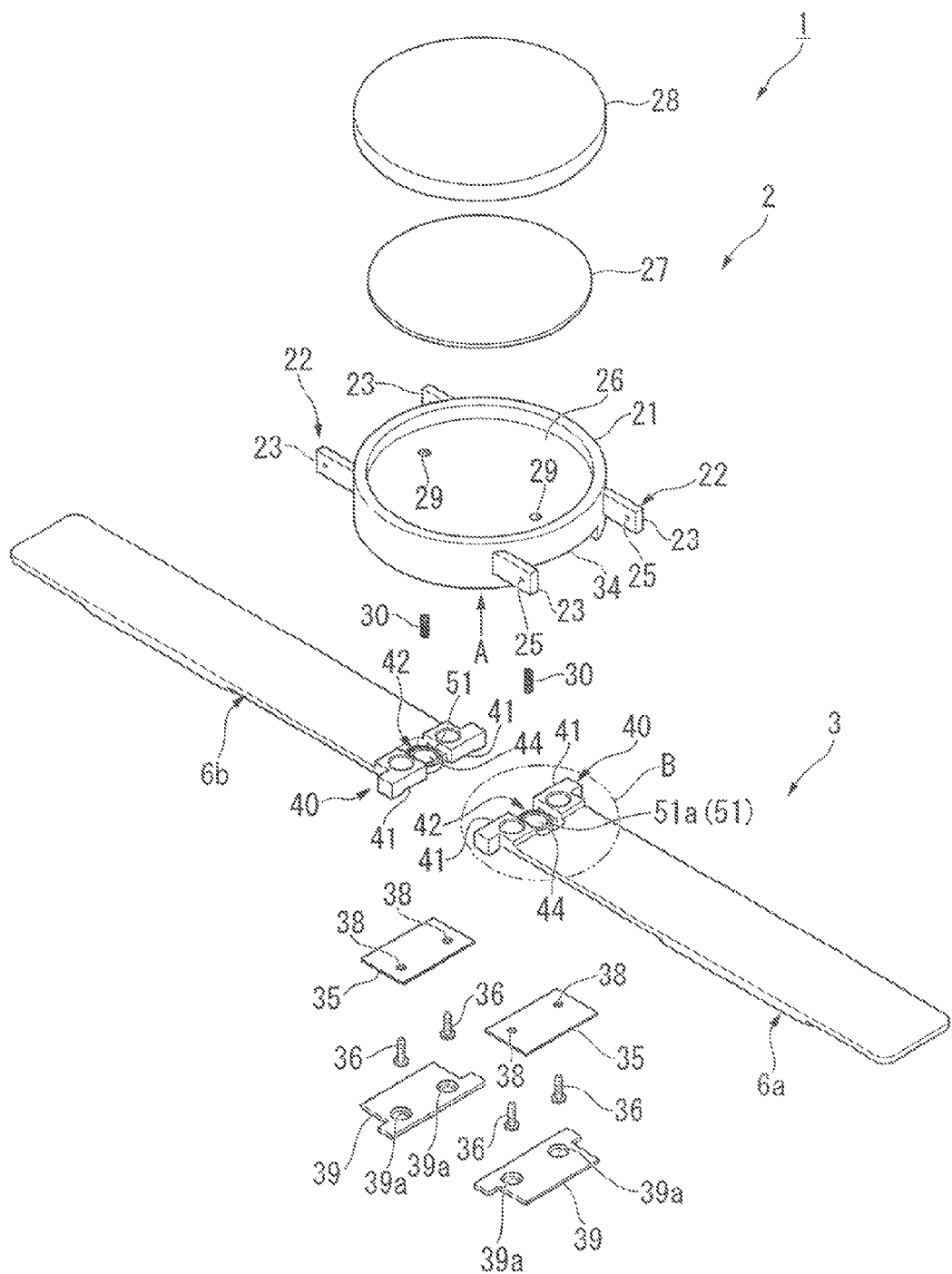
FIG. 4 is an exploded perspective view illustrating a main body portion and a heartbeat detection portion according to the first embodiment of the present invention.
Figure 5:
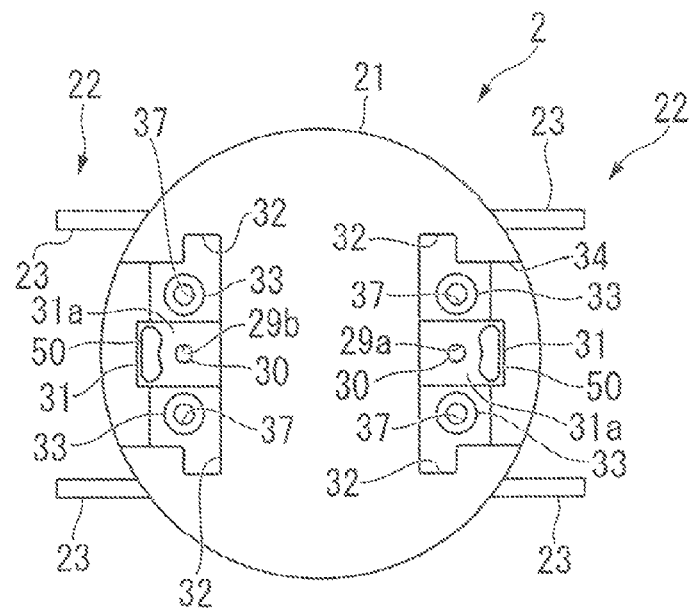
FIG. 5 is a diagram viewed from an arrow A of FIG. 4.
Figure 6:
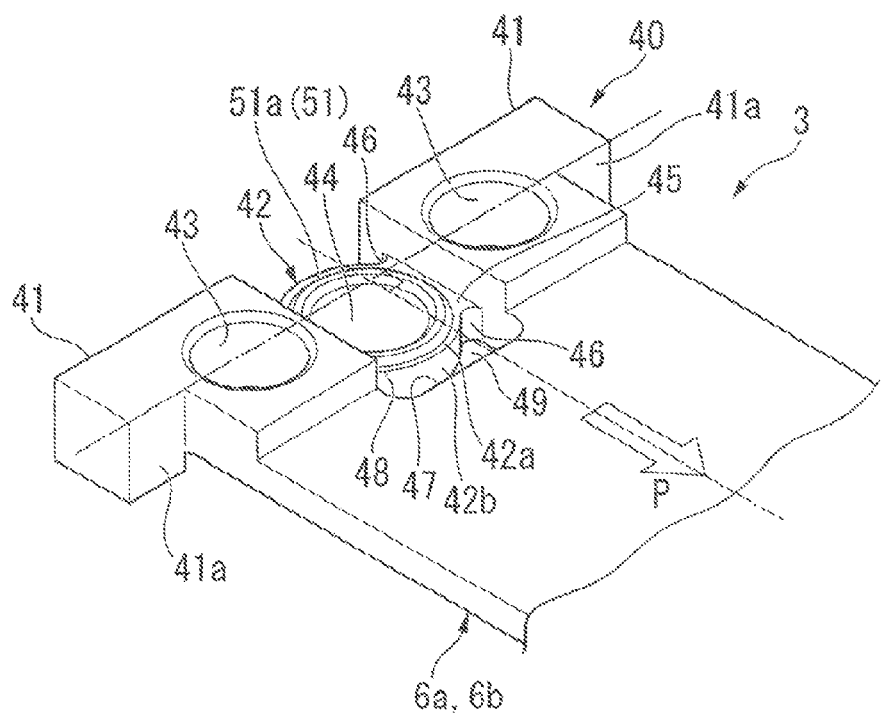
FIG. 6 is an enlarged view of a B portion of FIG. 4.
Figure 7:
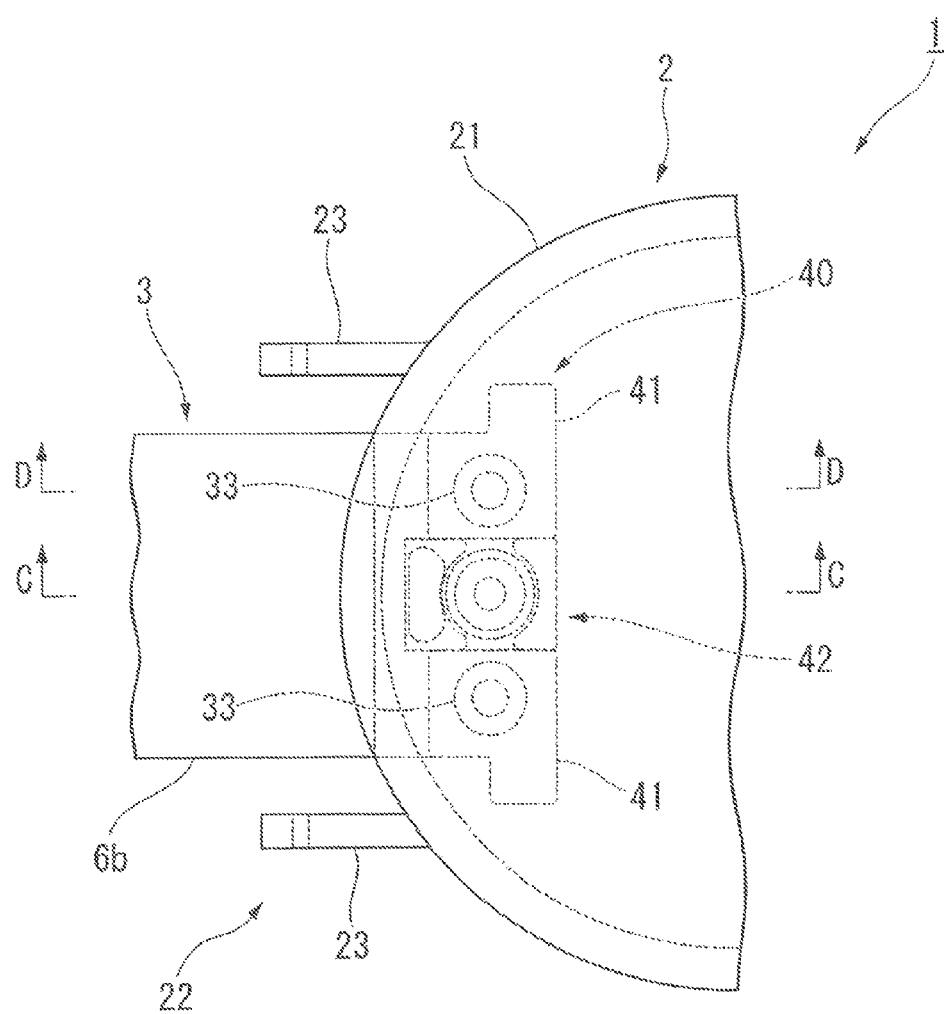
FIG. 7 is a partial plan view illustrating the main body portion and the heartbeat detection portion according to the first embodiment of the present invention.
Figure 8:
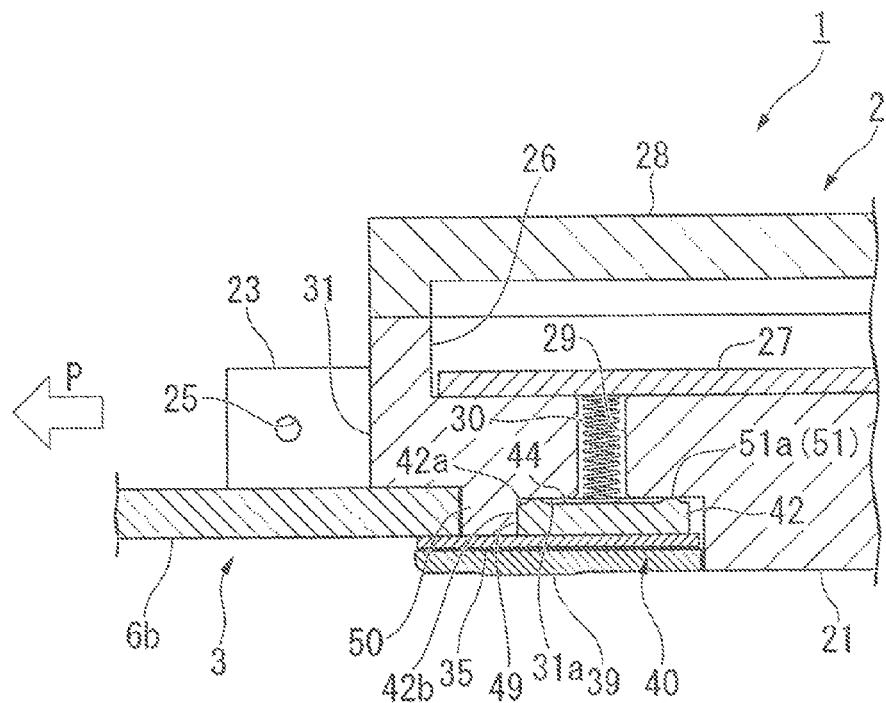
FIG. 8 is a cross-sectional view taken along the line C-C of FIG. 7.
Figure 9:
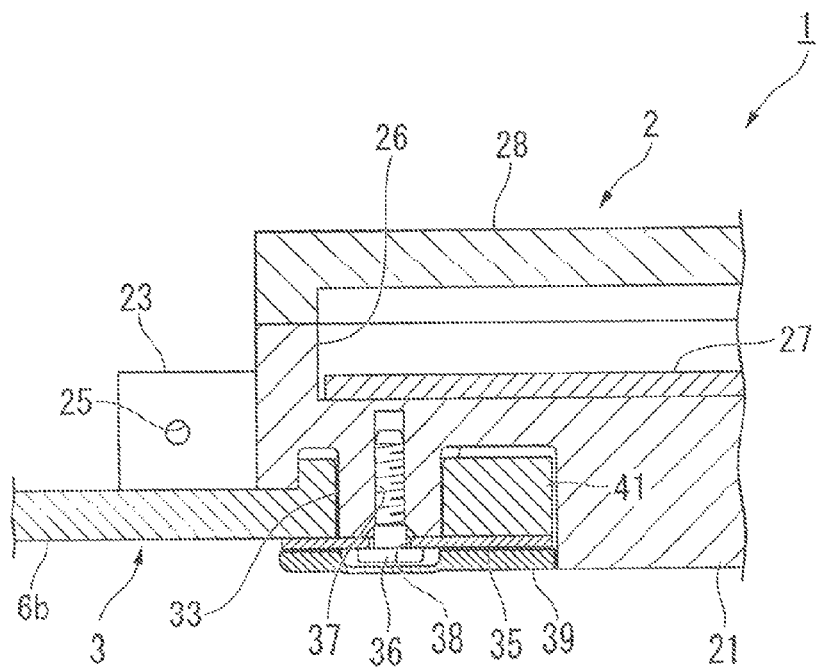
FIG. 9 is a cross-sectional view taken along the line D-D of FIG. 7.

FIG. 4 is an exploded perspective view illustrating the main body portion 2 and the heartbeat detection portion 3, FIG. 5 is a diagram viewed from an arrow A of FIG. 4, FIG. 6 is an enlarged view of a B portion of FIG. 4, FIG. 7 is a partial plan view illustrating the main body portion 2 and the heartbeat detection portion 3, FIG. 8 is a cross-sectional view taken along the line C-C of FIG. 7, and FIG. 9 is a cross-sectional view taken along the line D-D of FIG. 7.

As shown in FIGS. 3 to 9, the main body portion 2 includes a lower case 21 which is in a substantially disk shape. The lateral portions of the lower case 21 are respectively provided with connection members 22 for connecting the strap attaching and detaching members 12 and the main body portion 2 at both sides centered on the radial middle of the lower case 21.

The connection member 22 is constituted by a pair of support walls 23 and 23, formed upright from the lateral portion of the lower case 21, which face each other in the circumferential direction, and a shaft 24 provided so as to be laid between the support walls 23 and 23. The tip of the shaft 24 is configured to freely come in and out, and a through hole 25 capable of receiving the tip of the shaft 24 is formed in a place corresponding to the shaft 24 between the support walls 23 and 23.

Thereby, the shaft 24 is engaged with the support walls 23 and 23, and both 23 and 24 are integrated with each other. The hook portion 12b of the strap attaching and detaching member 12 is configured to be engageable with the shaft 24, and the main body portion 2 and the fixing band 4 is configured to be disengageable with each other.

In addition, in the front side of the lower case 21, a concave portion 26 is formed in the central large portion. A detection circuit board 27 is received in the concave portion 26. The detection circuit board 27 formed in substantially a disk shape so as to correspond to the shape of the concave portion 26. In addition, the detection circuit board 27 includes a wireless transmission portion and a transmitter circuit (all not shown), and performs wireless communication on the basis of a signal detected by the heartbeat detection portion 3.

Further, the concave portion 26 of the lower case 21 is provided with an upper case 28 so as to block an opening of the concave portion 26. The upper case 28 is formed in substantially a disk shape so as to correspond to the shape of the concave portion 26, and the diameter thereof is set so as to be substantially identical to the diameter of the lower case 21.

Meanwhile, each of the shapes of the lower case 21, the detection circuit board 27, and the upper case 28 is not limited to a substantial disk shape, and various shapes can be adopted. For example, the lower case 21, the detection circuit board 27, and the upper case 28 can also be formed so that the external shapes thereof are substantially rectangular when seen in a plan view.

In addition, through holes 29 and 29 passing through in the thickness direction close to each connection member 22 are formed in the concave portion 26 of the lower case 21, and a conductive member 30 is inserted into the through holes 29 and 29. The conductive member 30 is to electrically connect the detection circuit board 27 to the heartbeat detection portion 3, and is formed by, for example, a coil spring or the like.

Further, on the back side of the lower case 21, a positional displacement prevention convex portion 31 is integrally formed in an area corresponding to the through hole 29. The positional displacement prevention convex portion 31 is to prevent positional displacement of the main body portion 2 and the heartbeat detection portion 3 in a predetermined direction, and is formed in a substantially rectangular shape in cross-section so as to be elongated along the extension direction (horizontal direction in FIG. 5) of the strap 8. The through hole 29 passes through the positional displacement prevention convex portion 31 in the thickness direction.

In addition, a pair of first receiving concave portions 32 and 32, which are substantially L-shaped when seen in plan view, for receiving the heartbeat detection portion 3 in the lower case 21 side are respectively formed on both sides of the positional displacement prevention convex portion 31 in the short-side direction. A positional displacement prevention protrusion 33 for preventing positional displacement between the main body portion 2 and the heartbeat detection portion 3 in a predetermined direction is disposed upright integrally with the first receiving concave portion 32. A female screw portion 37 is engraved in the positional displacement prevention protrusion 33. A bolt 36 described later is threaded into the female screw portion 37, and is configured to be capable of fastening and fixing the heartbeat detection portion 3 to the main body portion 2.

Further, a second receiving concave portion 34 having a depth smaller than that of the first receiving concave portion 32 is formed at each connection member 22 side rather than the positional displacement prevention convex portion 31 and the first receiving concave portion 32. The second receiving concave portion 34 is also to receive the heartbeat detection portion 3 in the lower case 21 side, and is formed up to the lateral portion of the lower case 21. Thereby, the radial outside of the second receiving concave portion 34 is in an opened state, and the heartbeat detection portion 3 can be drawn into the lower case 21 from the outside.

The heartbeat detection portion 3 is placed in the first receiving concave portion 32 and the second receiving concave portion 34 which are formed in this manner, and a fixed reinforcing plate 35 is fastened and fixed to the lower case 21 using the bolt 36 from the top thereof, so that the main body portion 2 and the heartbeat detection portion 3 are integrated with each other. In the fixed reinforcing plate 35, a bolt insertion hole 38 is formed at a position corresponding to the female screw portion 37 engraved in the positional displacement prevention protrusion 33 of the lower case 21. The bolt 36 is inserted into the bolt insertion hole 38, and the fixed reinforcing plate 35 and the heartbeat detection portion 3 are fastened to each other.

In addition, a cover 39 is installed on the back side of the lower case 21 from the top of the fixed reinforcing plate 35. An opening 39a for avoiding interference with the head of the bolt 36 is formed in the cover 39. In addition, the cover 39 is formed so that the external shape thereof corresponds to the external shapes of the first receiving concave portion 32 and the second receiving concave portion 34. For this reason, the fixed reinforcing plate 35 and the bolt 36 can be completely covered by the cover 39, and the surface of the cover 39 and the surface of the lower case 21 can be disposed to be flush with each other, thereby allowing the aesthetics of the appearance to be improved.

The heartbeat detection portion 3 integrated with the main body portion 2 is constituted by a pair of electrodes 6a and 6b formed by belt-like conductive elastomer.

Herein, as the conductive elastomer, for example, conductive silicon rubber mixed with carbon black, conductive rubber mixed with carbon black, conductive polyurethane rubber mixed with carbon black, or the like can be used.

In each of the electrodes 6a and 6b, a connection structure 40 is integrally formed at one end on the main body portion 2 side in the long-side direction. The connection structure 40 is to connect each of the electrodes 6a and 6b to the main body portion 2 and to electrically connect the detection circuit board 27 received in the main body portion 2 to the electrodes 6a and 6b, and is formed from conductive elastomer similarly to the electrodes 6a and 6b.

In the connection structure 40, a pair of mechanical connection convex portions 41 and 41 formed in a substantially L-shape in cross-section so as to be capable of placing each of the first receiving concave portions 32 and 32 of the lower case 21, and an electrical connection circular plate 42 formed between the mechanical connection convex portions 41 and 41 and in an area corresponding to the positional displacement prevention convex portion 31 of the lower case 21 are formed integrally with each other.

In the mechanical connection convex portion 41, an insertion hole 43 capable of inserting the positional displacement prevention protrusion 33 is formed at a position corresponding to the positional displacement prevention protrusion 33 of the lower case 21.

The mechanical connection convex portions 41 and 41 are respectively placed in the first receiving concave portions 32 and 32 of the lower case 21, and the positional displacement prevention protrusion 33 of the lowercase 21 is inserted into each insertion hole 43 of the mechanical connection convex portions 41 and 41, thereby allowing displacement of the mechanical connection convex portion 41 with respect to the lower case 21 to be prevented.

On the other hand, the electrical connection circular plate 42 is disposed so that the radial center thereof is located coaxially with the through holes 29a and 29b formed in the positional displacement prevention convex portion 31 of the lower case 21. That is, the radially central portion of the electrical connection circular plate 42 is formed as an electrical connection portion 44 which comes into contact with the conductive member 30 inserted into the through hole 29, and in which the electrodes 6a and 6b and the detection circuit board 27 are electrically connected to each other.

In addition, a sealing portion 51 is integrally formed at an end face 42a of the electrical connection circular plate 42 on the main body portion 2 side so as to surround the periphery of the electrical connection portion 44. The sealing portion 51 is configured such that a seal main body 51a which is formed in a substantially triangular shape in cross-section is formed in a substantially circular-ring shape when seen in plan view so as to surround the periphery of the electrical connection portion 44.

Further, both sides of the electrical connection circular plate 42 are connected to the mechanical connection convex portions 41 through a connection portion 45 with the electrical connection portion 44 interposed therebetween. The connection portion 45 is integrally formed together with the mechanical connection convex portions 41 and the electrical connection circular plate 42. Both sides thereof in the width direction are slightly resected and constricted portions 46 are formed. The rigidity of the connection portion 45 is set to be weaker than that of the mechanical connection convex portion 41 or the electrical connection portion 44.

In addition, the thickness of the electrical connection circular plate 42 is set to be slightly smaller than the thickness of the electrodes 6a and 6b. Further, in the side end of the connection structure 40 of the electrodes 6a and 6b, a concave portion 47 of which the end is thrown in is formed in an area between the mechanical connection convex portions 41 and 41.

According to such a configuration, a fitting concave portion 48 into which the positional displacement prevention convex portion 31 of the lower case 21 is fitted is formed by the mechanical connection convex portion 41 and the electrical connection circular plate 42, and a slit 49 is formed between one end of the electrodes 6a and 6b in the long-side direction and the electrical connection circular plate 42.

The positional displacement prevention convex portion 31 of the lower case 21 is formed so as to be fitted into the fitting concave portion 48, and is formed so as to cover the slit 49. An end face 31a of the positional displacement prevention convex portion 31 and an end face 42a of the electrical connection circular plate 42 come close to each other. In addition, an insertion convex portion 50 capable of being inserted into the slit 49 is formed in the positional displacement prevention convex portion 31. Thereby, displacement of a relative position between the electrodes 6a and 6b and the main body portion 2 is prevented.

Based on such a configuration, when the connection structure 40 of each of the electrodes 6a and 6b is placed in the first receiving concave portion 32 and the second receiving concave portion 34 of the lower case 21, and the fixed reinforcing plate 35 is fastened and fixed to the lower case 21 from the top thereof using the bolt 36, the conductive member 30 provided to the lower case 21 and the electrical connection portion 44 of the connection structure 90 come into contact with each other, and the conductive member 30 and the electrical connection portion 44 are electrically connected to each other. In addition, the sealing portion 51 formed in the periphery of the electrical connection portion 49 is pressed and squashed to the positional displacement prevention convex portion 31 of the lower case 21. Thereby, sealing of the electrical connection portion 44 from the outside is secured reliably.

In this manner, after the heartbeat detection portion 3 constituted by the main body portion 2 and the electrodes 6a and 6b is integrally formed, the strap attaching and detaching member 12 of the fixing band 4 wound around the chest of the user U and the connection member 22 of the main body portion 2 are caused to be engaged with each other. Thereby, the mounting of the heartbeat measurement device 1 to the chest of the user U is completed. In a state where the heartbeat measurement device 1 is installed, each of the electrodes 6a and 6b is pressed down by the strap 8 from above. An electrocardiac signal generated in association with a heartbeat is detected by a pair of electrodes 6a and 6b. The detection circuit board 27 of the main body portion 2 wirelessly communicates the electro-cardiac signal detected by e pair of electrodes 6a and 6b.

Herein, the main body portion 2 and the electrodes 6a and 6b are separate from each other, each of the electrodes 6a and 6b is installed on the lower case 21 of the main body portion 2 through the connection structure 40, and the main body portion 2 and the electrodes 6a and 6b are formed integrally with each other. For this reason, there may be concern that it is difficult to cause a gap between the lower case 21 and the electrodes 6a and 6b not to be generated at all, and thus sweat of the human body or foreign substances infiltrate through this gap. When sweat of the human body or foreign substances infiltrate, the conductive member 30 may be corroded, or the state of the connection between the electrical connection portion 44 and the conductive member 30 may be deteriorated. However, since the sealing portion 51 is integrally formed in the periphery of the electrical connection portion 44, and sealing of the electrical connection portion 44 from the outside is secured, sweat of the human body or foreign substances are prevented from infiltrating.

(Operation of Mechanical Connection Convex Portion and Electrical Connection Circular Plate)

Next, an operation when the mechanical connection convex portion 41 and the electrical connection circular plate 42 receive a load due to external force P will be described with reference to FIGS. 5, 6, and 8.

Herein, the heartbeat measurement device 1 is configured such that the electrodes 6a and 6b constituting the heartbeat detection portion 3 are formed integrally with the main body portion 2 through the mechanical connection convex portion 41 and the electrical connection circular plate 42, and that the fixing band 4 is installed on the main body portion 2. For this reason, the fixing band 4 and the heartbeat detection portion 3 are separated from each other, and each of the electrodes 6a and 6b is pressed down to the chest of the user U by the strap 8 from the top thereof. Thus, it is possible to prevent the external force P such as tension from being applied to each of the electrodes 6a and 6b.

However, even in such a configuration, it is also considered that external force is applied to each of the electrodes 6a and 6b. Hereinafter, operations in a case where external force in the tensile direction is applied to the electrodes 6a and 6b will be described.

As shown in FIGS. 5, 6, and 8, when external force P in the tensile direction is applied to the electrodes 6a and 6b, a load is transmitted to the connection structure 40 formed integrally with one end of the electrodes 6a and 6b in the long-side direction. More specifically, a load is transmitted to the mechanical connection convex portion 41 formed integrally with the electrodes 6a and 6b. At this time, the direction of a load on the mechanical connection convex portion 41 is a direction of the electrodes 6a and 6b in the long-side direction.

Herein, the mechanical connection convex portion 41 is placed in the first receiving concave portion 32 of the lower case 21, and the positional displacement prevention protrusion 33 of the lower case 21 is inserted into each insertion hole 43 of the mechanical connection convex portions 41 and 41, thereby allowing displacement of the mechanical connection convex portion 41 with respect to the lower case 21 to be prevented from occurring. For this reason, a load on the mechanical connection convex portion 41 is received by a sidewall 41a of the mechanical connection convex portion 41 on the side of a direction in which the external force P is applied, the first receiving concave portion 32, and the positional displacement prevention protrusion 33, and is further received in the lower case 21. In addition, a peripheral wall 42b of the electrical connection circular plate 42 receives a load of the external force P together with the insertion convex portion 50 of the lower case 21.

In addition to this, the electrical connection circular plate 42 connected to the mechanical connection convex portion 41 through the connection portion 45 is disposed between each of the mechanical connection convex portions 41 and 41, and the array direction of the mechanical connection convex portions 41 and 41 and the electrical connection circular plate 42 becomes a direction intersecting substantially at a right angle to the direction of a load on the mechanical connection convex portion 41 (see FIG. 6). That is, the array direction of the insertion holes 43 and 43 formed in each of the mechanical connection convex portions 41 and 41 and the electrical connection circular plate 42 becomes a direction intersecting substantially at a right angle to the direction of the load on the mechanical connection convex portion 41. Further in other words, the relative positional relationship between each of the mechanical connection convex portions 41 and 41 and the electrical connection circular plate 42 is not arranged alongside the direction of the load on the mechanical connection convex portion 41.

Moreover, a constricted portion 46 is formed in the connection portion 45, and the rigidity of the connection portion 45 is set to be weaker than that of the mechanical connection convex portion 41 or the electrical connection portion 44. For this reason, the connection portion 45 is easily elastically deformed, and the load on the mechanical connection convex portion 41 is not easily transmitted to the electrical connection circular plate 42.

Therefore, according to the above-mentioned first embodiment, the heartbeat detection portion 3 and the fixing band 4 are separated from each other. Therefore, while the external force P in the tensile direction is prevented from being applied to the electrodes 6a and 6b, it is possible to stabilize the state of the connection between the electrical connection portion 44 of the electrical connection circular plate 42 and the conductive member 30 even when the external force P is applied to the electrodes 6a and 6b.

In addition, since the main body portion 2 and the heartbeat detection portion 3 are formed detachably to the fixing band 4, it is possible to easily perform cleaning of only the fixing band 4. Thus, it is possible to reliably prevent defects from occurring to the electrical parts such as the electrodes 6a and 6b, the conductive member 30, and the electrical connection portion 44.

Thus, it is possible to prevent the defective detection of the heartbeat measurement device 1 from occurring while securing good maintenance of the heartbeat measurement device 1.

In addition, the mechanical connection convex portion 41 and the electrical connection circular plate 42 are connected through the connection portion 45 having smaller rigidity than those stated above. Therefore, when a load is applied to the mechanical connection convex portion 41, the connection portion 45 is easily elastically deformed, thereby allowing the load to be absorbed. Moreover, since the mechanical connection convex portion 41, the electrical connection circular plate 42, and the connection portion 45 are formed from conductive elastomer and thus are easily elastically deformed, the load is easily absorbed by the mechanical connection convex portion 41 or the connection portion 45. For this reason, it is possible to more reliably suppress the application of the external force P to the electrical connection portion 44.

In addition to this, since the sidewall 41a of the mechanical connection convex portion 41 receives the load due to the external force P, and the peripheral wall 42b of the electrical connection circular plate 42 receives the load due to the external force P, it is possible to more reliably suppress transmission of the external force P to the electrical connection portion 44.

Meanwhile, in the above-mentioned first embodiment, a case has been described in which in mounting the heartbeat measurement device 1 to the chest of the user U, the fixing band 4 is wound around the chest of the user U, and then the strap attaching and detaching member 12 of the fixing band 4 and the connection member 22 of the main body portion 2 are caused to be engaged with each other. However, without being limited thereto, for example, the strap attaching and detaching member 12 of the fixing band 4 and the connection member 22 of the main body portion 2 may be caused to be engaged with each other, and then the heartbeat measurement device 1 may be mounted by winding the fixing band 4 around the chest of the user U.

In addition, in the above-mentioned first embodiment, a case has been described in which the conductive member 30 for electrically connecting the detection circuit board 27 to the electrical connection portion 44 is formed by, for example, a coil spring or the like. However, without being limited thereto, a pin or the like formed by, for example, a conductive material may be used instead of the coil spring.

Further, in the above-mentioned first embodiment, a case has been described in which the connection structure 40 causes the sidewall 41a of the mechanical connection convex portion 41 and the peripheral wall 42b of the electrical connection circular plate 42 to have a role of the wall receiving the load due to the external force P. However, without being limited thereto, the heartbeat detection portion 3 may be provided with the wall receiving the load due to the external force P separately from the mechanical connection convex portion 41 or the electrical connection circular plate 42.

In the above-mentioned first embodiment, a case has been described in which the electrical connection circular plate 42 is provided with the sealing portion 51. However, without being limited thereto, the main body portion 2 side may be provided with the sealing portion 51.

In addition, in the above-mentioned first embodiment, a case has been described in which the array direction of the mechanical connection convex portion 41 and the electrical connection circular plate 42, that is, the array direction of the insertion holes 43 and 43 formed in each of the mechanical connection convex portions 41 and 41 and the electrical connection circular plate 42 becomes a direction intersecting substantially at a right angle to the direction of the load on the mechanical connection convex portion 41. However, without being limited thereto, the relative positional relationship between each of the mechanical connection convex portions 41 and 41 and the electrical connection circular plate 42 is preferably set so as not to be arranged alongside the direction of the load on the mechanical connection convex portion 41. Hereinafter, a more specific aspect will be described.

(Modified Example of First Embodiment)

Figure 10:
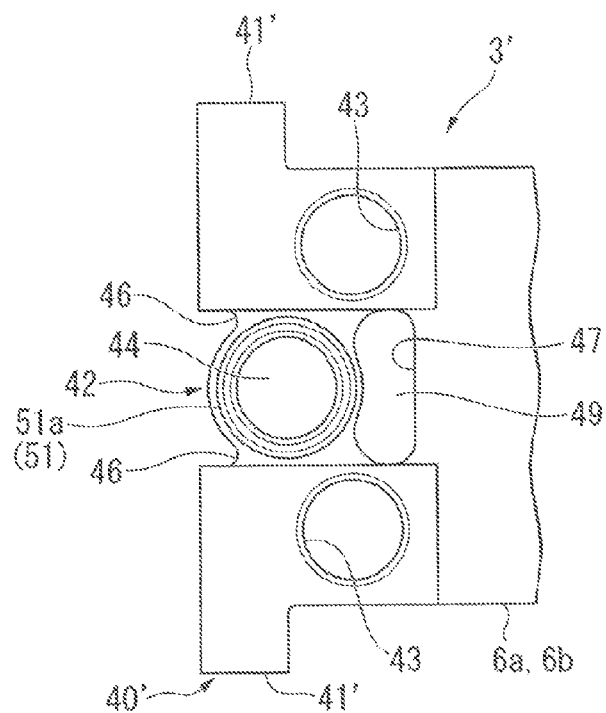
FIG. 10 is a plan view illustrating a heartbeat detection portion according to a modified example in the first embodiment of the present invention.

FIG. 10 is a plan view illustrating a heartbeat detection portion 3' according to a modified example of the first embodiment. Meanwhile, the same components as those of the above-mentioned first embodiment are designated by the same reference signs, and description thereof will be omitted (the same is true of the following embodiment).

As shown in the same drawing, in a connection structure 40' constituting the heartbeat detection portion 3', mechanical connection convex portions 41' and 41' placed in each of the first receiving concave portions 32 and 32 of the lower case 21 are formed so as to be further elongated along the long-side direction of the electrodes 6a and 6b than those in the above-mentioned first embodiment.

The insertion hole 43 formed in each of the mechanical connection convex portions 41' and 41' is formed displaced toward the opposite side to the main body portion 2 by a size in which the mechanical connection convex portion 41' of the first modified example is further extended out toward the opposite side (right side in FIG. 10) to the main body portion 2 than the mechanical connection convex portion 41 of the above-mentioned first embodiment. Displacement toward the opposite side to the main body portion 2 side is, in other words, displacement toward the direction (see FIG. 6) in which the external force P applied to the electrodes 6a and 6b acts.

Herein, the position of the insertion hole 43 is displaced toward the direction in which the external force P acts, so that the positional displacement prevention protrusion 33 inserted into the insertion hole 43 is formed displaced toward the direction in which the external force P acts. In this manner, the positions of the insertion hole 43 of the mechanical connection convex portion 41' and the positional displacement prevention protrusion 33 of the lower case 21 are displaced toward the direction in which the external force P acts, so that the distances between the insertion hole 43, the positional displacement prevention protrusion 33, and the electrical connection circular plate 42 become larger than those in the above-mentioned first embodiment.

Therefore, according to the above-mentioned modified example of the first embodiment, the external force P cannot be easily transmitted to the electrical connection circular plate 42.

Second Embodiment

Heartbeat Measurement Device

Next, reference will be made to FIG. 1 to describe a second embodiment of the present invention on the basis of FIGS. 11 to 16.

Figure 11:
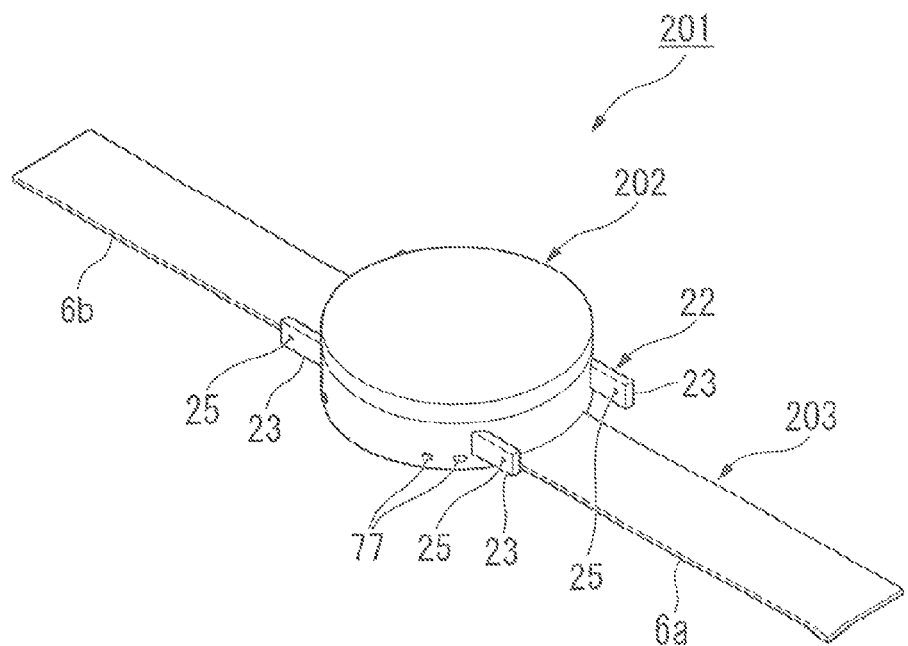
FIG. 11 is a perspective view illustrating a main body portion and a heartbeat detection portion according to a second embodiment of the present invention.
Figure 12:
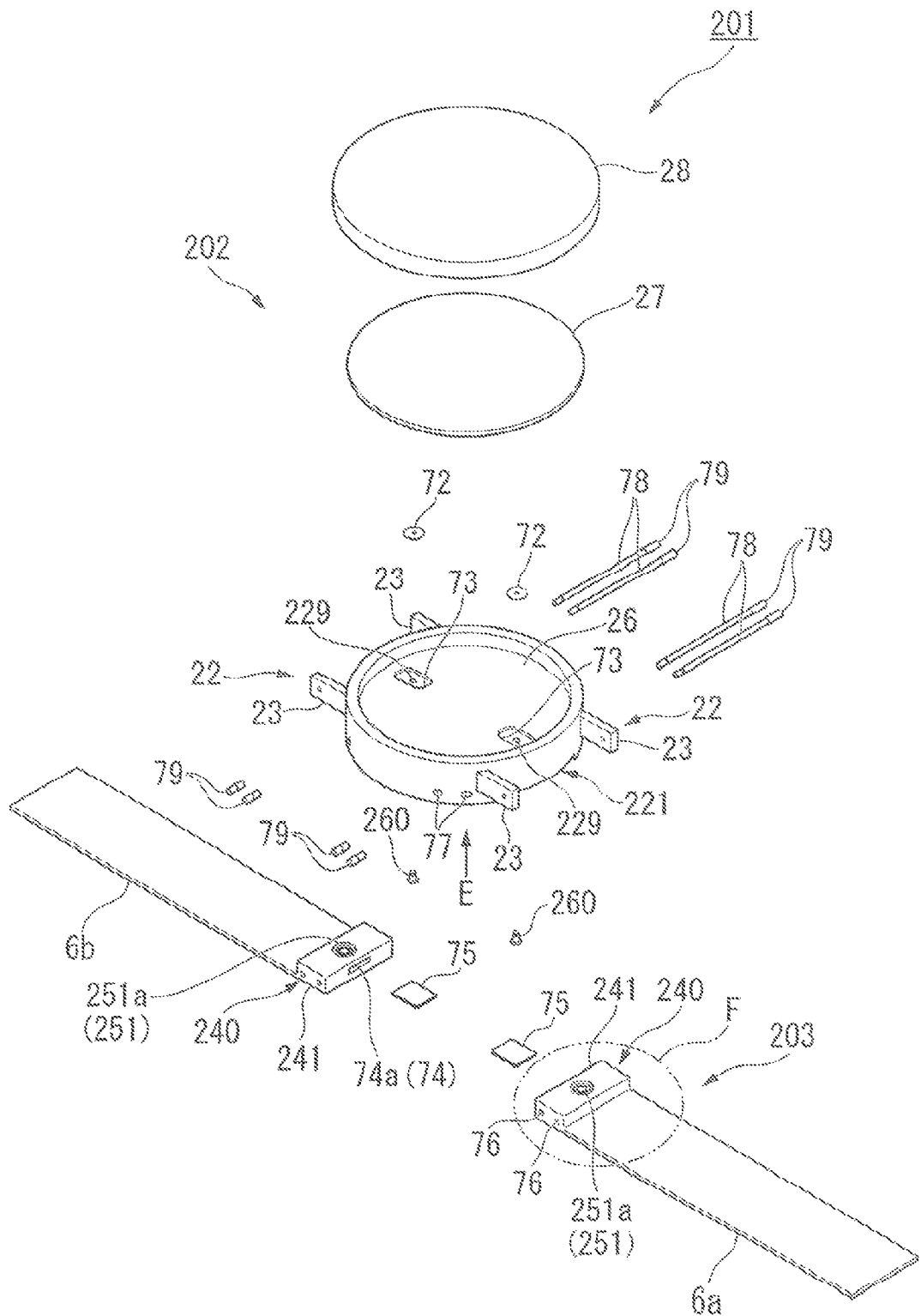
FIG. 12 is an exploded perspective view illustrating the main body portion and the heartbeat detection portion according to the second embodiment of the present invention.
Figure 13:
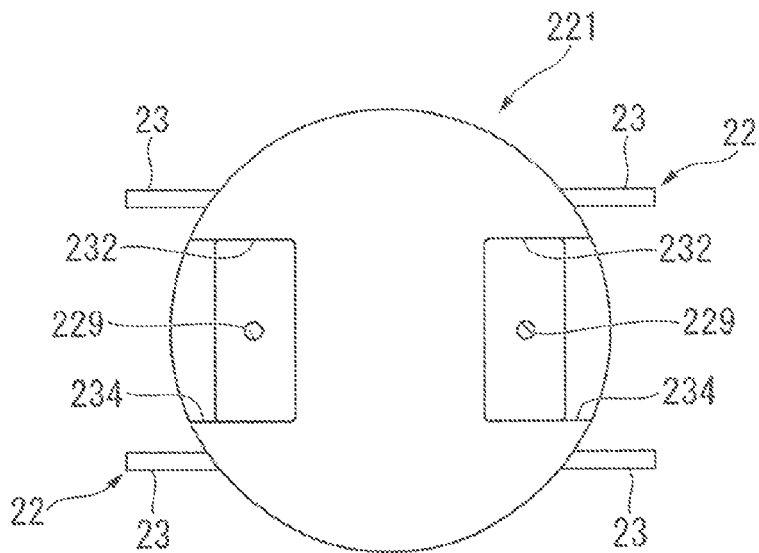
FIG. 13 is a diagram viewed from an arrow E of FIG. 12.
Figure 14:
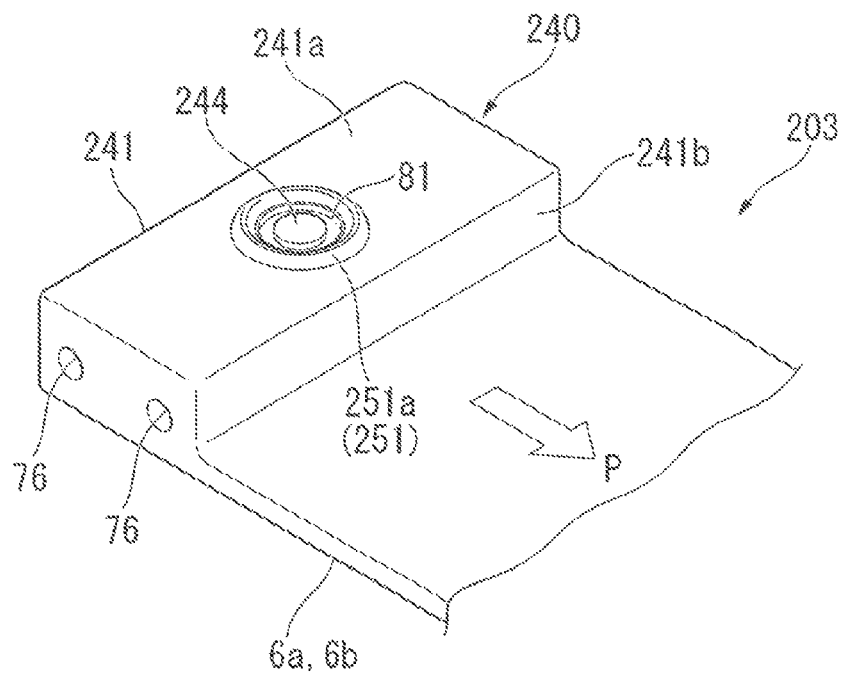
FIG. 14 is an enlarged view of an F portion of FIG. 12.
Figure 15:
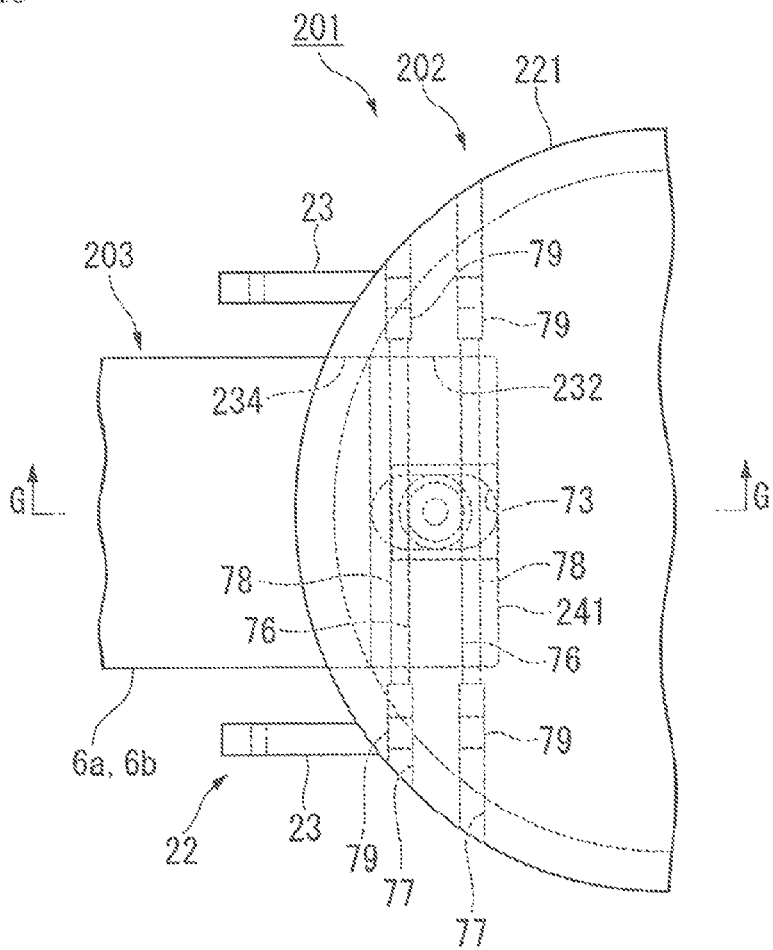
FIG. 15 is a partial plan view illustrating the main body portion and the heartbeat detection portion according to the second embodiment of the present invention.
Figure 16:
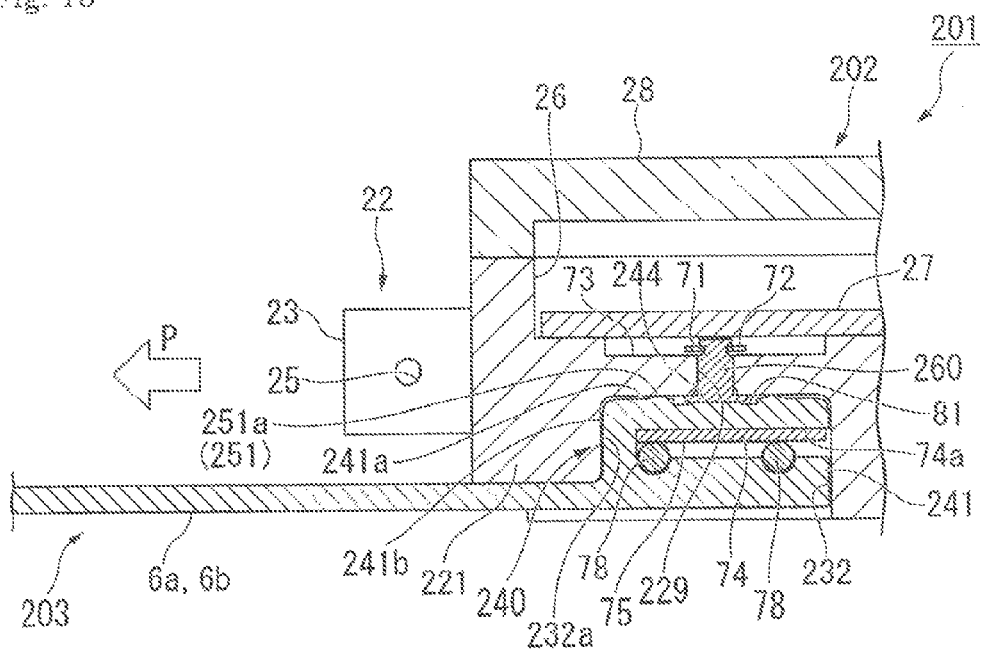
FIG. 16 is a cross-sectional view taken along the line G-G of FIG. 15.

FIG. 11 is a perspective view illustrating a main body portion 202 and a heartbeat detection portion 203 which constitute a heartbeat measurement device 201 according to the second embodiment, FIG. 12 is an exploded perspective view illustrating the main body portion 202 and the heartbeat detection portion 203 which constitute the heartbeat measurement device 201, FIG. 13 is a diagram viewed from an arrow E of FIG. 12, FIG. 14 is an enlarged view of an F portion of FIG. 12, FIG. 15 is a partial plan view illustrating the main body portion 202 and the heartbeat detection portion 203, and FIG. 16 is a cross-sectional view taken along the line G-G of FIG. 15.

As shown FIGS. 1, 11, and 12, in the second embodiment, the heartbeat measurement device 201 includes the main body portion 202, the heartbeat detection portion 203 formed integrally with the main body portion 202, and the fixing band 4 which mounts the main body portion 202 and the heartbeat detection portion 203 to the chest of the user U. The following basic configuration of the embodiment is the same as the above-mentioned first embodiment: the fixing band 4 and the main body portion 202 are detachable with each other through the strap attaching and detaching member 12 and the connection member 22; the heartbeat detection portion 203 and the fixing band 4 are separated from each other; the heartbeat detection portion 203 includes a pair of electrodes 6a and 6b; when the heartbeat measurement device 201 is mounted, the electrodes 6a and 6b are pressed down by the strap 8 from above; the main body portion 202 includes a lower case 221, the detection circuit board 27 provided to the concave portion 26 formed in the lower case 221, and the upper case 28 provided so as to block the concave portion 26; the detection circuit board 27 and each of the electrodes 6a and 6b are electrically connected to each other, and the like.

Herein, the difference between the first embodiment and the second embodiment is that a connection structure between the main body portion 2 and the heartbeat detection portion 3 according to the first embodiment and a connection structure between the main body portion 202 and the heartbeat detection portion 203 according to the second embodiment are different from each other.

More specifically, as shown in FIGS. 11 to 16, through holes 229 and 229 passing through in the thickness direction close to each connection member 22 are formed in the concave portion 26 of the lower case 221. A conductive pin 260 is inserted into the through hole 229 from the back side of the lower case 221.

A retaining ring groove 71 is formed on the tip of the conductive pin 260. After the conductive pin 260 is inserted into the through hole 229, a retaining ring 72 is mounted to the retaining ring groove 71. Thereby, the conductive pin 260 is prevented from falling out from the through hole 229. In addition, in the concave portion 26 of the lower case 221, a counter-boring portion 73 receiving the retaining ring 72 is formed in an area corresponding to the through hole 229, and the tip of the conductive pin 260 can be prevented from protruding from the concave portion 26 of the lower case 221.

Further, on the back side of the lower case 221, a first receiving concave portion 232 is formed in an area corresponding to the through hole 229. The first receiving concave portion 232 is to receive the heartbeat detection portion 203, and is formed in a substantially rectangular shape when seen in plan view so as to be elongated in the width direction of the electrodes 6a and 6b constituting the heartbeat detection portion 203.

In addition, a second receiving concave portion 234 having a depth smaller than that of the first receiving concave portion 232 is formed on each connection member 22 side rather than the first receiving concave portion 232. The second receiving concave portion 234 extends up to the lateral portion of the lower case 221 with the same width as the width of the first receiving concave portion 232 in the long-side direction. Thereby, the radial outside of the second receiving concave portion 234 is in an opened state. The electrodes 6a and 6b are disposed in the second receiving concave portion 234.

Meanwhile, the width of the first receiving concave portion 232 and the width of the second receiving concave portion 234 may not be set to be the same as each other.

On the other hand, in each of the electrodes 6a and 6b, a connection structure 240 is integrally formed at one end on the main body portion 202 side in the long-side direction. The connection structure 240 is to connect each of the electrodes 6a and 6b to the main body portion 202, and to electrically connect the detection circuit board 27 received in the main body portion 202 to the electrodes 6a and 6b. The connection structure 240 includes a mechanical connection convex portion 241 formed in a substantially rectangular shape in cross-section so as to be elongated in the width direction of each of the electrodes 6a and 6b, as corresponding to the first receiving concave portion 232 of the lower case 221. The mechanical connection convex portion 241 is formed integrally with one end of each of the electrodes 6a and 6b in the long-side direction, and is received in the first receiving concave portion 232, so that the main body portion 202 and the heartbeat detection portion 203 are integrated with each other.

In the mechanical connection convex portion 241, a reinforcing plate receiving groove 74 having an opening 74a is formed at the end face on the main body portion 202 side (right side in FIG. 16). A reinforcing plate 75 is received in the reinforcing plate receiving groove 74

In addition, in the mechanical connection convex portion 241, two through holes 76 and 76 on the convex portion side passing through along the width direction of the electrodes 6a and 6b are disposed in parallel along the long-side direction of the electrodes 6a and 6b. Further, each through hole 76 on the convex portion side is formed so as to be in communication with the reinforcing plate receiving groove 74.

In addition, in the lower case 221, when the mechanical connection convex portion 241 is received in the first receiving concave portion 232, a through hole 77 on the case side is formed at a position corresponding to the through hole 76 on the convex portion side of the mechanical connection convex portion 241. The internal diameter of the through hole 77 on the case side is set to be slightly larger than the internal diameter of the through hole 76 on the convex portion side.

A fixing pin 78 is inserted into the through hole 76 on the convex portion side and the through hole 77 on the case side. The length of the fixing pin 78 is larger than the length of the mechanical connection convex portion 241 in the long-side direction, and is set to a length in which the fixing pin does not protrude from the lateral portion of the lower case 221. A fixing pipe 79 is fitted and fixed onto both ends of the fixing pin 78.

Herein, the diameter of the fixing pin 78 is set to be substantially identical to the internal diameter of the through hole 76 on the convex portion side. In addition, the diameter of the fixing pipe 79 is set to be substantially identical to the internal diameter of the through hole 77 on the case side. That is, after the mechanical connection convex portion 241 is received in the first receiving concave portion 232 of the lower case 221, a fixing pin 78 is inserted into the through hole 76 on the convex portion side through the through hole 77 on the case side, and the fixing pipe 79 inserted into the through hole 77 on the case side is fitted and fixed onto both ends of the fixing pin 78.

Since the diameter of the fixing pipe 79 is set to be larger than the internal diameter of the through hole 76 on the convex portion side, the fixing pipe 79 is fitted and fixed onto both ends of the fixing pin 78, and thus the movement of the fixing pin 78 to the falling-out direction is regulated. In addition, the fixing pin 78 is inserted into the through hole 76 on the convex portion side and the through hole 77 on the case side, so that each of the electrodes 6a and 6b is fixed to the lower case 221 through the fixing pin 78.

In addition, since the through hole 76 on the convex portion side is formed so as to be in communication with the reinforcing plate receiving groove 74, the reinforcing plate 75 is placed on the fixing pin 78 in a state where the fixing pin 78 is inserted into the through hole 76 on the convex portion side. The groove width of the mechanical connection convex portion 241 in the thickness direction in the reinforcing plate receiving groove 74 is set so that the reinforcing plate 75 is brought into contact with the inner wall of the reinforcing plate receiving groove 74, in a state where the reinforcing plate 75 is placed on the fixing pin 78. Thereby, the rigidity of an end face 241a of the mechanical connection convex portion 241 on the main body portion 202 side (upper side in FIGS. 14 and 16) is increased.

In addition, in the end face 241a of the mechanical connection convex portion 241, a ring-shaped groove 81 is formed in the periphery of a position corresponding to the conductive pin 260, and the inside of the groove 81 is used as an electrical connection portion 244. That is, the electrical connection portion 244 is provided in the central portion of the end face 241a of the mechanical connection convex portion 241. In addition, a ring-shaped sealing portion 251 is integrally formed in the periphery of the groove 81. That is, the sealing portion 251 is integrally formed so as to surround the periphery of the electrical connection portion 244. The sealing portion 251 is a component in which a seal main body 251a formed in a substantially triangular shape in cross-section is formed in a substantially circular-ring shape when seen in plan view so as to surround the periphery of the electrical connection portion 244.

Herein, when the electrodes 6a and 6b are installed on the lower case 221, the electrical connection portion 244 and the sealing portion 251 are pressed and squashed to the bottom of the first receiving concave portion 232 of the lower case 221. Since the rigidity of the end face 241a of the mechanical connection convex portion 241 is increased by the reinforcing plate 75, the sealing portion 251 formed so as to protrude from the end face 241a of the mechanical connection convex portion 241 is easily squashed. In addition, since the ring-shaped groove 81 is formed in the end face 241a of the mechanical connection convex portion 241, and the inside of the groove 81 is used as the electrical connection portion 244, the electrical connection portion 244 is also easily squashed.

In addition, when the heartbeat measurement device 201 is mounted on the user U, each of the electrodes 6a and 6b are pressed down by the strap 8, and thus there is a low possibility of external force being applied directly. However, when external force P in the tensile direction is applied to the electrodes 6a and 6b, a load is transmitted to the connection structure 240 formed integrally with one end of each of the electrodes 6a and 6b in the long-side direction.

At this time, a load toward the radial outside acts on the lower case 221 through the fixing pin 78 connecting the mechanical connection convex portion 241 of the connection structure 240 to the lower case 221. Further, the mechanical connection convex portion 241 is received in the first receiving concave portion 232 formed in the lower case 221. Therefore, when the external force P in the tensile direction is applied to the electrodes 6a and 6b, the sidewall 241b of the mechanical connection convex portion 241 on the electrodes 6a and 6b side presses an inside surface 232a of the first receiving concave portion 232. In other words, the sidewall 241b on the side of a direction in which the external force P of the mechanical connection convex portion 241 is applied receives a load due to the external force P, and transmits the load to the inside surface 232a of the first receiving concave portion 232. Thereby, the lower case 221 receives the external force P acting on the electrodes 6a and 6b.

On the other hand, since the electrical connection portion 244 for electrically connecting the detection circuit board 27 to the electrodes 6a and 6b is located further at the front side than the fixing pin 78, a load due to the external force P is not easily transmitted. That is, since the electrical connection portion 244 is disposed at a position displaced in the direction perpendicular to the direction of a load of the external force P acting on the fixing pin 78 with respect to the fixing pin 78, a load due to the external force P is not easily transmitted. For this reason, even when the external force P is applied to the electrodes 6a and 6b, it is possible to stabilize the state of the connection between the electrical connection portion 244 and the conductive pin 260.

Therefore, according to the above-mentioned second embodiment, it is possible to accomplish the same effect as that of the above-mentioned first embodiment. That is, the main body portion 202 and the heartbeat detection portion 203 are formed integrally with each other, and the main body portion 202 and the heartbeat detection portion 203 are formed detachably to the fixing band 4, thereby allowing good maintenance of the heartbeat measurement device 201 to be secured.

In addition, the sealing portion 251 is provided in the periphery of the electrical connection portion 244, so that it is possible to reliably prevent sweat from the human body or foreign substances from infiltrating from the outside to the electrical connection portion 244, and to prevent the defective connection between the electrical connection portion 244 and the conductive pin 260 from occurring.

Further, even when the external force P is applied to the electrodes 6a and 6b, the state of the connection between the electrical connection portion 244 and the conductive pin 260 can be stabilized, and thus it is possible to stabilize detection accuracy of the heartbeat measurement device 201, and to provide products having high reliability.

Meanwhile, in the above-mentioned second embodiment, a case has been described in which the conductive pin 260 is used in order to electrically connect the detection circuit board 27 to the electrical connection portion 244. However, the pin may be a conductive member without being limited thereto. For example, it is also possible to use a coil spring or the like instead of the conductive pin 260.

In addition, in the above-mentioned second embodiment, a case has been described in which the sidewall 241b of the mechanical connection convex portion 241 is caused to have a role of the wall receiving the load due to the external force P. However, without being limited thereto, the heartbeat detection portion 203 may be provided with the wall receiving the load due to the external force P separately from the mechanical connection convex portion 241.

Further, in the above-mentioned second embodiment, a case has been described in which the mechanical connection convex portion 241 is provided with the sealing portion 251. However, the sealing portion 251 may be provided on the main body portion 202 side, without being limited thereto.

In the above-mentioned second embodiment, a case has been described in which the ring-shaped groove 81 is formed on the end face 241a of the mechanical connection convex portion 241, and the inside of the groove 81 is used as the electrical connection portion 244. Such a configuration can also be applied to the electrical connection portion 44 of the above-mentioned first embodiment. That is, a ring-shaped groove may be formed on the end face 42a of the electrical connection circular plate 42, and the inside of the groove may be used as the electrical connection portion 44.

Further, the present invention is not limited to the above-mentioned embodiments, and various changes may be added to the above-mentioned embodiments without departing from the scope of the present invention.

For example, in the above-mentioned embodiment, a case has been described in which the main body portions 2 and 202 and the heartbeat detection portions 3 and 203 are formed integrally with each other in the heartbeat measurement devices 1 and 201 that measure a heart rate of the user U as a biological information detection device, and the sealing portions 51 and 251 are provided in the periphery of the electrical connection portions 44 and 244 for electrically connecting the main body portions 2 and 202 and the heartbeat detection portions 3 and 203. However, such a configuration is not only applied to the heartbeat measurement devices 1 and 201, but also can be applied to various biological information detection devices. For example, as the biological information detection devices, the configuration of the above-mentioned embodiments and the modified examples can be applied to devices that measure blood pressure, body temperature, myogenic potential and the like.

In addition, in the above-mentioned embodiment, a case has been described in which in order to mount the heartbeat measurement devices 1 and 201 to the chest of the user U, the fixing band 4 is provided, and the fixing band 4 and the main body portions 2 and 202 are formed detachably with each other through the strap attaching and detaching member 12 and the connection member 22. However, without being limited thereto, the fixing band 4 and the main body portions 2 and 202 may be detachable with each other, and configurations other than the strap attaching and detaching member 12 and the connection member 22 may be used. For example, a pair of support walls 23 and 23 and the shaft 24 constituting the connection member 22 may be integrally formed in the lower cases 21 and 221.

What is claimed is:

1. A biological information detection device comprising:
   a device main body;
   a biological signal detection portion formed integrally with the device main body, the biological signal detection portion having an electrode for contacting a biological surface of a human body; and
   a fixing portion configured to mount the device main body and the biological signal detection portion to a human body without the fixing portion being directly attached to the biological signal detection portion;

wherein the device main body and the biological signal detection portion are integrally connected by a mechanical connection portion that mechanically connects the device main body and the biological signal detection portion to each other, and by an electrical connection portion that electrically connects the device main body and the electrode of the biological signal detection portion to each other; and wherein the mechanical connection portion and the electrical connection portion are positioned relative one another so as not to be arranged alongside a load direction of an external force acting on the mechanical connection portion.

2. The biological information detection device according to claim 1, wherein the electrical connection portion and the mechanical connection position are positioned relative one another so that a sidewall of the mechanical connection portion is configured to receive a load due to an external force acting on the mechanical connection portion to thereby suppress transmission of the external force to the electrical connection portion.

3. The biological information detection device according to claim 1, further comprising a deformable portion disposed between the mechanical connection portion and the electrical connection portion.

4. The biological information detection device according to claim 1, wherein the biological signal detection portion is formed of a conductive elastomer serving as the electrode.

5. The biological information detection device according to claim 1, wherein the mechanical connection portion and the electrical connection portion are positioned relative one another so that an array direction of the mechanical connection portion and the electrical connection portion is a direction intersecting the load direction of an external force acting on the mechanical connection portion.

6. The biological information detection device according to claim 5, wherein the array direction of the mechanical connection portion and the electrical connection portion intersects the load direction substantially at a right angle.

7. The biological information detection device according to claim 1, wherein the mechanical connection portion and the electrical connection portion are integrally connected together through an intermediate connection portion having a lower rigidity that the mechanical connection portion or the electrical connection portion.

8. The biological information detection device according to claim 7, wherein the intermediate connection portion is integrally formed together with the mechanical connection portion and the electrical connection portion.

9. The biological information detection device according to claim 7, wherein a constricted portion is formed in the intermediate connection portion so that when a load is applied to the mechanical connection portion due to an external force, the intermediate connection portion is easily elastically deformed, thereby allowing the load to be absorbed and application of the external force to the electrical connection portion to be suppressed.

10. A biological information detection device comprising:
a main body portion;
a biological signal detection portion integral with the main body portion and having at least one electrode configured to be brought into contact with a biological surface of a human body for detecting a biological signal;
a connection structure provided at a terminal end of the electrode for integrally connecting the biological signal detection portion to the main body portion, the connection structure having a mechanical connection portion that mechanically connects the main body portion to the biological signal detection portion, an electrical connection portion that electrically connects the main body portion to the electrode of the biological signal detection portion, and at least one intermediate connection portion integrally connecting the mechanical connection portion and the electrical connection portion to one another, the intermediate connection portion having a lower rigidity than that of the mechanical connection portion or the electrical connection portion so that when a load is applied to the mechanical connection portion due to an external force, the intermediate connection portion is easily elastically deformed, thereby allowing the load to be absorbed and application of the external force to the electrical connection portion to be suppressed; and
a mounting portion for removably mounting the main body portion and the biological signal detection portion to a human body to detect a biological signal of the human body.

11. The biological information detection device according to claim 10, wherein the mechanical connection portion comprises a convex portion protruding from a surface of the electrode, and the electrical connection portion comprises a circular plate integrally connected to the convex portion through the intermediate connection portion.

12. The biological information detection device according to claim 10, wherein the intermediate connection portion has a constricted portion that further facilitates elastic deformation of the intermediate connection portion when a load is applied to the mechanical connection portion due to an external force.

13. The biological information detection device according to claim 10, wherein the mounting portion removably mounts the main body without the mounting portion being directly attached to the biological signal detection portion.

14. The biological information detection device according to claim 10, wherein the electrical connection portion and the mechanical connection portion are positioned relative one another so that a sidewall of the mechanical connection portion is configured to receive the load due to an external force acting on the mechanical connection.

15. The biological information detection device according to claim 10, wherein the biological signal detection portion is formed of a conductive elastomer serving as the electrode.

16. The biological information detection device according to claim 10, wherein the mechanical connection portion and the electrical connection portion are positioned relative one another so that an array direction of the mechanical connection portion and the electrical connection portion is a direction intersecting the load direction of an external force acting on the mechanical connection portion.

17. The biological information detection device according to claim 16, wherein the array direction of the mechanical connection portion and the electrical connection portion intersects the load direction substantially at a right angle.

18. The biological information detection device according to claim 10, wherein the at least one electrode of the biological signal detection portion comprises a pair of electrodes each having the connection structure for integrally connecting the electrodes to the main body portion so as to extend from respective opposite sides thereof.

19. The biological information detection device according to claim 18, wherein the at least one intermediate connection portion comprises a pair of intermediate connection portions; and wherein the mechanical connection portion comprises a pair of convex portions, and the electrical connection portion comprises a circular plate disposed between and connected to each of the convex portions through the respective intermediate connection portions.

20. The biological information detection device according to claim 19, wherein each of the convex portions, the circular plate, and each of the respective intermediate connection portions is formed from a conductive elastomer.

* * * * *